United States Patent [19]

Van Eyck et al.

[11] 3,997,554
[45] Dec. 14, 1976

[54] N,N-DI (CARBONYL CHLORIDES) OF N,N'-ALKYLENE UREAS

[75] Inventors: Michael J. Van Eyck, Midland, Mich.; Laurence I. Peterson, Doylestown, Pa.

[73] Assignee: The Dow Chemical Company, Midland, Mich.

[22] Filed: Aug. 25, 1975

[21] Appl. No.: 607,404

Related U.S. Application Data

[63] Continuation-in-part of Ser. No. 555,464, March 5, 1975, abandoned.

[52] U.S. Cl. .................. 260/309.7; 260/239.3 R; 260/251 R
[51] Int. Cl.[2] ...................................... C07D 233/38
[58] Field of Search ................ 260/309.7, 239.3 R, 260/251 R

[56] References Cited
UNITED STATES PATENTS

| | | | |
|---|---|---|---|
| 3,275,618 | 9/1966 | Tilley et al. .................. | 270/309.7 |
| 3,304,327 | 2/1967 | Rapaelian et al. ........... | 260/239.3 R |
| 3,506,551 | 4/1970 | Beck et al. .................... | 260/251 R |

OTHER PUBLICATIONS

Zav'yalov et al. Izv. Akad. Nauk SSSR, Ser. Khim. 1972, (10), pp. 2308–2312.
Laboratoires Bruneau & Cie, Chem. Abst., vol. 62, Cols. 574–575 (1965).

Ulrich et al., J. Org. Chem., vol. 29, pp. 2401–2404, (1964).

*Primary Examiner*—Natalie Trousof
*Attorney, Agent, or Firm*—David H. Fifield

[57] ABSTRACT

Compounds of the formula

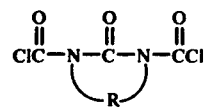

wherein —R— is di-, tri- or tetramethylene which may bear from 1 to 8 $C_1$–$C_3$ alkyl substituents, and a process for their preparation wherein a reactant of the formula

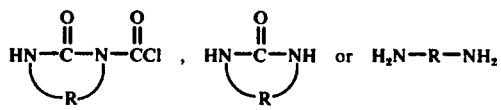

is contacted, at reaction temperature, with $COCl_2$. For example, 2-imidazolidone is contacted with phosgene to form N,N'-bis(carbonyl chloride)-2-imidazolidone. The compounds may be condensed with polyols, polythiols or polyamines to form useful resins or pyrolyzed to give alkylene diisocyanates.

4 Claims, No Drawings

N,N-DI(CARBONYL CHLORIDES) OF N,N'-ALKYLENE UREAS

CROSS-REFERENCE TO RELATED APPLICATION

This is a continuation-in-part of our copending application Ser. No. 555,464 filed Mar. 5, 1975, now abandoned.

BACKGROUND OF THE INVENTION

1. Field of the Invention

The invention is directed to N,N'-di(carbonyl chloride) 5, 6 and 7 membered N,N'-alkylene ureas and a process for the preparation of these compounds.

2. Prior Art

J. N. Tilley et al., U.S. Pat. No. 3,275,618 (1966), teach the preparation of alkylene diisocyanates and intermediates which are N,N'-alkylene allophanyl chlorides. These heterocyclic 1,3-diazo-N-monocarbonyl chlorides are produced by reacting N,N'-alkylene ureas in about equimolar amounts with phosgene. They further teach that excess phosgene can be used but will not react with the hydrogen atom of the second nitrogen atom of the heterocycle to form dicarbonyl chlorides.

SUMMARY OF THE INVENTION

Disclosed are compounds represented by the formula

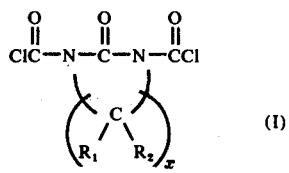

(I)

and a process for their preparation where reactant (I) of the formula

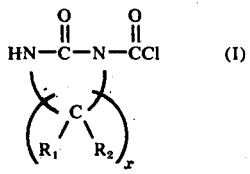

(I)

wherein $R_1$ and $R_2$ are independently, each occurrence, hydrogen or alkyl of 1 to about 3 carbon atoms and $x$ is 2, 3 or 4, is contacted at a reaction temperature above about 100° C with phosgene. In the process, the reactants are preferably contacted at a reaction temperature between about 120° and 160° C.

The novel compounds may be reacted with polyols, polythiols or polyamines to form polyesters, polythioesters or polyamides.

DETAILED DESCRIPTION OF THE INVENTION

Reactants and Products:

The desired product is prepared by contacting reactant (I) with phosgene above about 100° C. Reactant (I) is a 5, 6 or 7 membered N,N'-alkylene allophanyl chloride of the type described by Tilley et al. in U.S. Pat. No. 3,275,618. For example, N-monocarbonyl chlorides of ethylene urea, propylene urea (1,2-propylene urea), trimethylene urea (1,3-propylene urea), tetramethylene urea (1,4-butylene urea) or the like may be employed as reactant (I). N,N'-Alkylene ureas other than those described here may be produced by the method of Schweitzer in *J. Org. Chem.* 15:471 (1950) by contacting a properly substituted alkylene diamine, of the desired

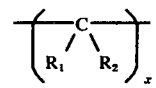

alkylene unit, with urea. They may then be converted to N-monocarbonyl chlorides by contacting with about an equimolar amount of phosgene according to the method of Tilley et al.

When phosgene is contacted with trimethylene urea-N-carbonyl chloride $$(ClC\overset{O}{\overset{\|}{-}}N-CO-NHCH_2CH_2CH_2)$$

at a reaction temperature above about 100° C the product will be the compound represented by the formula

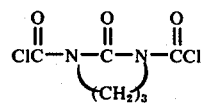

Similarly, when phosgene and 2-imidazolidone-N-carbonyl chloride are reacted, a product of the formula

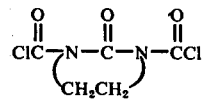

will be produced. Other representative novel compounds are those of formula (II)

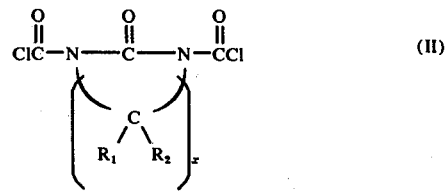

(II)

wherein

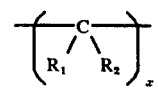

is:

—CH₂CH₂CH₂CH₂—; —CH₂C(—CH₃)₂CH₂—;
—CH₂CH(—CH₃)—; —CH(—CH₃)CH(—CH₃)—;
—CH₂CH(—CH₃)CH₂—; —CH(—CH₃)CH₂CH(—CH₃)—;
—CH(—C₂H₅)CH₂—; —CH₂CH(—C₃H₇)CH₂—
or the like. Preferred are compounds where in

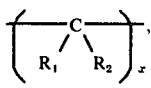

the only alkyl substituents on the normal alkylene chain are one or two methyl groups. Most preferred are compounds wherein when $x$ is 3 or 4, $R_1$ and $R_2$ are both hydrogen, each occurrence, and when $x$ is 2 both $R_1$'s are hydrogen, one $R_2$ is hydrogen and the other $R_2$ is methyl or hydrogen. I.e.

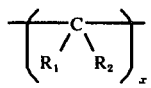

is most preferably ethylene, 1,2-propylene, trimethylene or tetramethylene.

Reaction Conditions:

The reaction temperature at which the process is carried out is suitably above about 100° C and preferably between about 120°–160° C. It appears that the reaction of phosgene with an alkylene urea takes place in a stepwise fashion; the first —COCl radical reacting with one nitrogen atom in the alkylene urea at a temperature above about 0° C and the second —COCl radical reacting at above about 100° C. Such a stepwise addition reaction may be employed to prepare the invention compounds.

Alternatively, phosgene and an N,N'-alkylene urea of desired structure are mixed at below the reaction temperature in greater than about a 1:1 phosgene-urea molar ratio, the temperature is raised to above about 100° C, preferably to between about 120°–160° C, and both amido nitrogens are phosgenated without having to prepare the monocarbonyl chloride separately.

Contact time for the reactants is not critical. Completion of the replacement of active hydrogen atoms by carbonyl chloride groups may conveniently be noted by the cessation of the evolution of gaseous HCl from the reaction mixture or by IR or NMR spectroscopy. Ordinarily, the total reaction is substantially complete in about 1–8 hours.

An excess amount of phosgene is preferably maintained at all times once the reactants have been brought to the reaction temperature. The phosgene:(I) molar ratio is preferably at least about 1:1. Most preferably, phosgene will be present in about 50%–100% excess, i.e., a phosgene:(I) molar ratio of at least 2:1. These ratios are based on the amount of (I) initially charged.

Conveniently, the entire quantity of phosgene to be employed will be added to the reaction vessel first with (I) being added thereafter. In this manner, an excess of phosgene is maintained at all times. It is also possible to first add a quantity of phosgene, for example 20% of the total to be added, then simultaneously add equivalent amounts of the reactants until all of (I) has been added with an excess of phosgene present.

As it is generally desirable to maintain the reactants in the liquid phase, phosgene may be dissolved in a quantity of inert solvent and reactant (I) subsequently added to that mixture. Suitable solvents are those such as chlorobenzene, ortho-dichlorobenzene, 1,2,4-trichlorobenzene, sulfolane, diphenyl ether, nitrobenzenes, chlorotoluenes, tetrahydrofuran, dialkyl ethers, and the like. The quantity of solvent employed may be such as to enable the reaction mixture to be easily handled at all times. Suitably the solvent will be present in excess such that reactant (I) is about 1 to 25% of the weight of the solvent and preferably from about 5 to 10% of the weight of the solvent.

The reaction is suitably carried out at autogenous pressure under an inert atmosphere. Reduction in reaction time may be obtained by maintaining the reaction mixture in the liquid phase. This can be accomplished by selection of suitable temperatures and pressures at which the reaction may be carried out. The pressure is preferably anywhere from the autogenous pressure of the system up to about 25 atm. and most preferably from 10 to 20 atm. Since phosgene is volatile at elevated temperatures, superatmospheric pressures are maintained to keep the mixture in the preferred liquid phase.

The products, generally solids under standard conditions, may be recovered by boiling off the solvent and any excess phosgene, redissolving in benzene or another suitable solvent and recrystallizing therefrom.

Utility:

The novel compounds of the invention may be condensed with aliphatic or aromatic polyols or polythiols to form useful polyester or polythioester resins or with polyamines to form useful polyamide resins. The novel compounds may also be pyrolyzed at about 200°–400° C. to yield alkylene diisocyanates, for example, ethylene diisocyanate, which are known comonomers useful in the production of polyurethane resins.

SPECIFIC EMBODIMENTS OF THE INVENTION

Example 1: Two Step Phosgenation

Into a 1 liter, 5-necked flask equipped with stirrer, gas inlet tube, thermometer, reflux condenser and a graduated addition funnel, 300 ml. of orthodichlorobenzene were added. The reaction vessel was heated to about 90° C. and phosgene was bubbled into the orthodichlorobenzene for about 30 minutes to saturate the solvent with phosgene while the system was maintained at reflux conditions by the dry ice condenser. About 43 g. (0.5 mole) of ethylene urea was dissolved in approximately 300 ml. of ortho-dichlorobenzene at a temperature of about 90° C. and this mixture was placed in the addition funnel which was equipped to maintain a temperature of about 90° C. While the flow of phosgene to the ortho-dichlorobenzene in the flask was maintained at about 1.5 g./min., the ethylene urea-dichlorobenzene mixture was added dropwise to the reaction vessel with the observed evolution of HCl gas. After the addition of ethylene urea was complete, the flow of phosgene was maintained and the temperature of the reaction vessel was raised to about 150° C. Reaction conditions were maintained until the reaction was complete as indicated by infrared spectroscopy of samples taken from the reaction medium. The infrared spectrum of the solution showed carbonyl bands at about 1830 cm.$^{-1}$, 1730 cm.$^{-1}$ and 1850 cm.$^{-1}$, the intensities being in respectively decreasing order. There was only a weak remnant of the amido bands of the monocarbonyl chloride or ethylene urea which occur between about 3300–3500 cm.$^{-1}$. The entire reaction time was less than 5 hours.

Example 2: Phosgenation Above 100° C.

About 50 ml. of a preheated (180° C.) 2.85 M solution of ethylene urea in nitrobenzene was added to an agitated, refluxing solution of 500 ml. of nitrobenzene at 150° C. which had been saturated with phosgene. The nitrobenzene-phosgene mixture contained more than the stoichiometric amount of phosgene needed to react with both amido groups of the ethylene urea reactant.

The temperature of the mixture was thereafter maintained at about 150° C. and 1 ml. grab samples were withdrawn at intervals of 3, 5 and 50 minutes after the initial addition of ethylene urea. These samples were purged with nitrogen while hot to remove any unreacted phosgene. Infrared spectroscopy showed complete conversion of ethylene urea to the monocarbonyl chloride in the 3 minute sample and the 5 minute sample gave a spectrum identical to that of the 3 minute sample. The 50 minute sample's spectrum indicated essentially complete conversion of ethylene urea and its monocarbonyl chloride to the dicarbonyl chloride as evidenced by the sample's characteristic IR spectrum with bands at about 1830, 1850 and 1725 cm.$^{-1}$, in order of decreasing intensity respectively. The characteristic band at about 3420 cm.$^{-1}$, representing the amido group of the monocarbonyl chloride, was only slightly visible while no band was discernible at about 3460 cm.$^{-1}$ where the absorption band characterizing ethylene urea's amido groups is normally found.

Example 3: Isolation and Recrystallization

In the manner of Example 1, ethylene urea was transformed into the dicarbonyl chloride derivative in the solvents sulfolane, chlorobenzene and trichlorobenzene at temperatures from about 50° to about 160° C.

The crude product was recovered as an orange-brown solid from which the pure N,N'-dicarbonyl chloride of ethylene urea was obtained by recrystallization from benzene at about 10° C. This pure product, an off-white amorphous solid, had a melting point of 92°-94° C. IR and NMR analyses confirmed the structure. Elemental analysis was as follows:

|  | C | H | N | Cl | (wt. %) |
|---|---|---|---|---|---|
| Calculated: | 28.5 | 1.9 | 13.3 | 33.6 | |
| Observed: | 28.7 | 2.1 | 13.9 | 31.9 | |

Example 4: Ethylenediamine and Phosgene

Excess phosgene was contacted with ethylenediamine at a relatively low temperature, forming N,N'-ethylene urea in situ. The temperature was raised to allow the excess phosgene to replace the amido nitrogen's hydrogen atoms with carbonyl chloride radicals, demonstrating the operability of a single batch process for preparation of the invention composition from an alkylenediamine precursor. Details are set out below.

A 1 liter, 5-necked flask was partially immersed in an ice bath at 5° C. and 1.8 mole of phosgene was introduced into the flask through a sparger tube over a period of 1 hour. 50 Ml. of sulfolane were then added to the reaction vessel. Thereafter, 0.25 mole of ethylenediamine in 150 ml. of sulfolane was pumped under the surface of the phosgene-sulfolane solution and 200 ml. more of sulfolane was added to the mixture. The temperature of the reactor was then slowly raised to about 165° C. over a period of about 4.5 hours. During the progress of the reaction, samples were taken at various time-temperature intervals and were analyzed by IR and nuclear magnetic resonance spectroscopy. Infrared analysis of the final dark brown product exhibited 3 characterisitic carbonyl peaks at approximately 1850, 1830 and 1730 cm.$^{-1}$. It was noted that the N-H absorption band at approximately 3355 cm.$^{-1}$ continually decreased and was essentially gone in Sample 6. The following table shows the time and temperature intervals at which the samples were taken.

TABLE II

| Sample No. | Reaction Time in Minutes | Reaction Temperature ° C. | Comments |
|---|---|---|---|
| 1 | 0 | 10 | Slurry of white solids formed immediately on contact of phosgene with ethylenediamine |
| 2 | 40 | 55 | Suspension of white particles |
| 3 | 110 | 90 | Yellow liquid, solids appear dissolved |
| 4 | 150 | 105 | Dark yellow liquid |
| 5 | 195 | 150 | Brown liquid |
| 6 | 240 | 160 | Dark brown, amido band absent in IR |
| 7 | 285 | 165 | Dark brown liquid |

We claim:
1. A compound represented by the formula

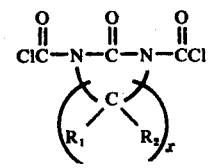

wherein $x$ is 2, 3 or 4 and $R_1$ and $R_2$ are independently, each occurrence, hydrogen or alkyl of from 1 to about 3 carbon atoms.

2. A compound of claim 1 wherein when $x$ is 3 or 4, $R_1$ and $R_2$ are both hydrogen, each occurrence, and when $x$ is 2 both $R_1$'s are hydrogen, one $R_2$ is hydrogen and the other $R_2$ is methyl or hydrogen.

3. The compound of claim 1 wherein $x$ is 2 and $R_1$ and $R_2$ are both hydrogen, each occurrence.

4. The compound of claim 1 wherein $x$ is 2, both $R_1$'s are hydrogen, one $R_2$ is methyl and the other $R_2$ is hydrogen.

* * * * *